United States Patent
Bender et al.

(10) Patent No.: US 9,563,896 B1
(45) Date of Patent: Feb. 7, 2017

(54) KINETIC TRACKING IN MANUFACTURING TO PREDICT AND PREVENT DEFECTS

(71) Applicant: International Business Machines Corporation, Armonk, NY (US)

(72) Inventors: Michael Bender, Rye Brook, NY (US); Rhonda L. Childress, Austin, TX (US); Michael J. Spisak, East Northport, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/946,176

(22) Filed: Nov. 19, 2015

(51) Int. Cl.
G01P 15/00 (2006.01)
G06Q 30/00 (2012.01)
A61B 5/11 (2006.01)

(52) U.S. Cl.
CPC .......... *G06Q 30/018* (2013.01); *G01P 15/003* (2013.01); *A61B 5/11* (2013.01); *A61B 5/1117* (2013.01); *G01P 15/001* (2013.01)

(58) Field of Classification Search
CPC .......... G01P 15/01; G01P 15/003; A61B 5/11; A61B 5/1117; A61B 5/68; A61B 5/6801; A61B 5/6802; A61B 5/6803
USPC .......................................................... 702/81
See application file for complete search history.

(56) References Cited

U.S. PATENT DOCUMENTS

| | | | |
|---|---|---|---|
| 8,674,810 B2 | 3/2014 | Uysal et al. | |
| 8,823,524 B2 | 9/2014 | Bradley et al. | |
| 8,920,345 B2 | 12/2014 | Greenberg et al. | |
| 2002/0198618 A1* | 12/2002 | Madden | B62D 65/02 700/101 |
| 2010/0241380 A1* | 9/2010 | Cookson | G06T 7/0004 702/84 |
| 2010/0270372 A1* | 10/2010 | Bae | G06Q 10/06 235/380 |
| 2011/0251865 A1* | 10/2011 | Yuen | G06Q 10/06 705/7.11 |
| 2012/0086809 A1* | 4/2012 | Lee | H04N 7/185 348/155 |

(Continued)

FOREIGN PATENT DOCUMENTS

| | | |
|---|---|---|
| CN | 104460670 A | 3/2015 |
| JP | 5702772 B2 | 4/2015 |

(Continued)

OTHER PUBLICATIONS

Trexler, The SHOP Tracking and Notification System, IEEE 1996.*

(Continued)

*Primary Examiner* — John Breene
*Assistant Examiner* — Lynda Dinh
(74) *Attorney, Agent, or Firm* — Terrile, Cannatti, Chambers & Holland, LLP; Stephen A. Terrile

(57) ABSTRACT

A system, method, and computer-readable medium for tracking manufacturing steps comprising: tracking kinetic movements of an assembler over a period of time to provide kinetic tracking information, the kinetic movements comprising product assembly movements; storing the kinetic tracking information in a kinetic tracking information repository; identifying a defect in an item manufactured during the period of time; and, analyzing the kinetic tracking information to determine whether the kinetic movements of the assembler contributed to the defect.

15 Claims, 4 Drawing Sheets

(56) References Cited

U.S. PATENT DOCUMENTS

| | | | |
|---|---|---|---|
| 2014/0143038 A1* | 5/2014 | Tropper | A61B 5/1118 705/14.19 |
| 2015/0044641 A1 | 2/2015 | Chauncey et al. | |
| 2015/0104757 A1 | 4/2015 | Moncrief et al. | |

FOREIGN PATENT DOCUMENTS

| | | |
|---|---|---|
| KR | 101525413 | 6/2015 |
| WO | 2014123419 A1 | 8/2014 |

OTHER PUBLICATIONS

R Lin et al., KBR's Automation Solutions for Increased Productivity and Safety in an Ammonia Plant, IPCOM000217727D, Feb. 2005.

D. Shvorin et al., Improving tennis player performance using system development interpretations methodology, International Journal of Quality Engineering and Technology, 4(3), 2014, pp. 225-242.

* cited by examiner

KINETIC TRACKING IN MANUFACTURING TO PREDICT AND PREVENT DEFECTS

BACKGROUND OF THE INVENTION

Field of the Invention

The present invention relates in general to the field of computers and similar technologies, and in particular to software utilized in this field. Still more particularly, it relates to a method, system and computer-usable medium for kinetic tracking in manufacturing to predict and prevent defects.

Description of the Related Art

It is known to communicate with and control many devices via the Internet. This communication and control is often referred to as the Internet of Things (IoT) and the devices are referred to as IoT devices. The IoT allows devices to be sensed and controlled remotely as well as to provide information based upon the type of IoT device across existing network infrastructure.

In many manufacturing environments, manual manufacturing steps (i.e., steps manually performed by an individual) can be prone to errors such as when the individual is tired or distracted and does not properly complete the manufacturing step (i.e., does not adhere to correct procedures). With many manufacturing environments, it can be difficult to correlate poor manufacturing techniques with poor product quality. With many manufacturing environments, it can be difficult to prevent or minimize manufacturing detects of products.

SUMMARY OF THE INVENTION

A system, method, and computer-readable medium are disclosed for tracking manufacturing steps comprising: tracking kinetic movements of an assembler over a period of time to provide kinetic tracking information, the kinetic movements comprising product assembly movements; storing the kinetic tracking information in a kinetic tracking information repository, identifying a defect in an item manufactured during the period of time; and, analyzing the kinetic tracking information to determine whether the kinetic movements of the assembler contributed to the defect.

BRIEF DESCRIPTION OF THE DRAWINGS

The present invention may be better understood, and its numerous objects, features and advantages made apparent to those skilled in the art by referencing the accompanying drawings. The use of the same reference number throughout the several figures designates a like or similar element.

DETAILED DESCRIPTION

Figure 1:
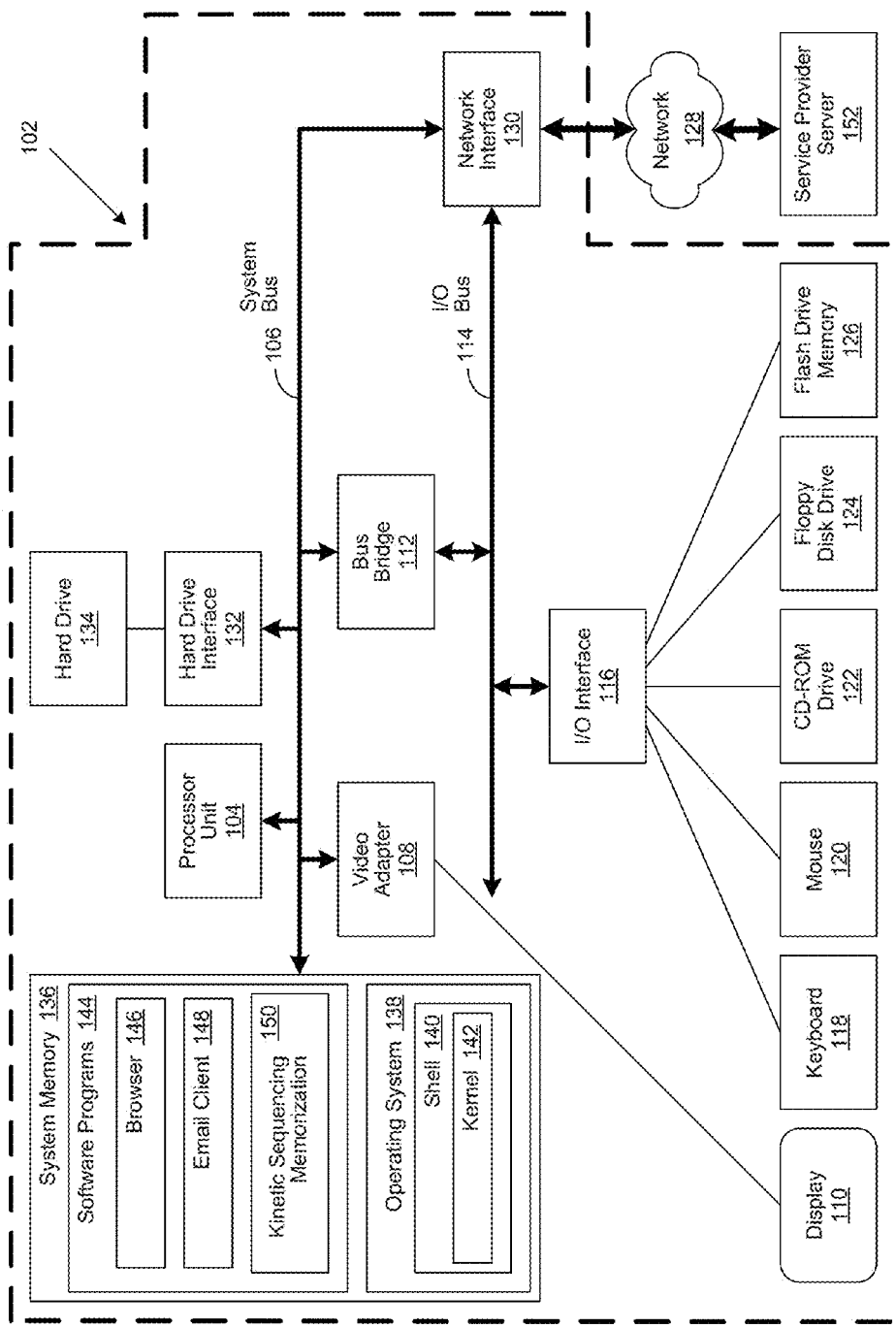
FIG. 1 depicts an exemplary client computer in which the present invention may be implemented.

A method, system and computer-usable medium are disclosed for a manufacturing tracking operation. The manufacturing tracking operation uses a sensor (such as an IoT type kinetic sensor) in a manufacturing environment where items are manually assembled. The sensors track repeated motions of the assembler. The sensors tracks the motion at all times and associates the tracking information to an item manufactured by the assembler. Quality control on the item is also associated with the assembler. The manufacturing tracking operation then applies analytics to determine whether certain motions are causing the defective parts. The manufacturing tracking operation also correlates certain identified motions with certain defects. Such a correlation allows remediated action to be applied to decrease manufacturing defects in future manufacturing operations. The correlation information can also be applied to training of other assemblers.

As will be appreciated by one skilled in the art, the present invention may be embodied as a method, system, or computer program product. Accordingly, embodiments of the invention may be implemented entirely in hardware, entirely in software (including firmware, resident software, microcode, etc.) or in an embodiment combining software and hardware. These various embodiments may all generally be referred to herein as a "circuit," "module," or "system." Furthermore, the present invention may take the form of a computer program product on a computer-usable storage medium having computer-usable program code embodied in the medium.

Any suitable computer usable or computer readable medium may be utilized. The computer-usable or computer-readable medium may be, for example, but not limited to, an electronic, magnetic, optical, electromagnetic, infrared, or semiconductor system, apparatus, or device. More specific examples (a non-exhaustive list) of the computer-readable medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, or a magnetic storage device. In the context of this document, a computer-usable or computer-readable medium may be any medium that can contain, store, communicate, or transport the program for use by or in connection with the instruction execution system, apparatus, or device.

Computer program code for carrying out operations of the present invention may be written in an object oriented programming language such as Java, Smalltalk, C++ or the like. However, the computer program code for carrying out operations of the present invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

Embodiments of the invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

FIG. 1 is a block diagram of an exemplary client computer 102 in which the present invention may be utilized. Client computer 102 includes a processor unit 104 that is coupled to a system bus 106. A video adapter 108, which controls a display 110, is also coupled to system bus 106. System bus 106 is coupled via a bus bridge 112 to an Input/Output (I/O) bus 114. An I/O interface 116 is coupled to I/O bus 114. The I/O interface 116 affords communication with various I/O devices, including a keyboard 118, a mouse 120, a Compact Disk-Read Only Memory (CD-ROM) drive 122, a floppy disk drive 124, and a flash drive memory 126. The format of the ports connected to I/O interface 116 may be any known to those skilled in the art of computer architecture, including but not limited to Universal Serial Bus (USB) ports.

Client computer 102 is able to communicate with a service provider server 152 via a network 128 using a network interface 130, which is coupled to system bus 106. Network 128 may be an external network such as the Internet, or an internal network such as an Ethernet Network or a Virtual Private Network (VPN). Using network 128, client computer 102 is able to use the present invention to access service provider server 152.

A hard drive interface 132 is also coupled to system bus 106. Hard drive interface 132 interfaces with a hard drive 134. In a preferred embodiment, hard drive 134 populates a system memory 136, which is also coupled to system bus 106. Data that populates system memory 136 includes the client computer's 102 operating system (OS) 138 and software programs 144.

OS 138 includes a shell 140 for providing transparent user access to resources such as software programs 144. Generally, shell 140 is a program that provides an interpreter and an interface between the user and the operating system. More specifically, shell 140 executes commands that are entered into a command line user interface or from a file. Thus, shell 140 (as it is called in UNIX®), also called a command processor in Windows®, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 142) for processing. While shell 140 generally is a text-based, line-oriented user interface, the present invention can also support other user interface modes, such as graphical, voice, gestural, etc.

As depicted, OS 138 also includes kernel 142, which includes lower levels of functionality for OS 138, including essential services required by other parts of OS 138 and software programs 144, including memory management, process and task management, disk management, and mouse and keyboard management. Software programs 144 may include a browser 146 and email client 148. Browser 146 includes program modules and instructions enabling a World Wide Web (WWW) client (i.e., client computer 102) to send and receive network messages to the Internet using HyperText Transfer Protocol (HTTP) messaging, thus enabling communication with service provider server 152. In various embodiments, software programs 144 may also include a manufacturing tracking module 150. In these and other embodiments, the manufacturing tracking module 150 includes code for implementing the processes described herein below. In one embodiment, client computer 102 is able to download the manufacturing tracking module 150 from a service provider server 152.

The hardware elements depicted in client computer 102 are not intended to be exhaustive, but rather are representative to highlight components used by the present invention. For instance, client computer 102 may include alternate memory storage devices such as magnetic cassettes, Digital Versatile Disks (DVDs), Bernoulli cartridges, and the like. These and other variations are intended to be within the spirit, scope and intent of the present invention.

Figure 2:
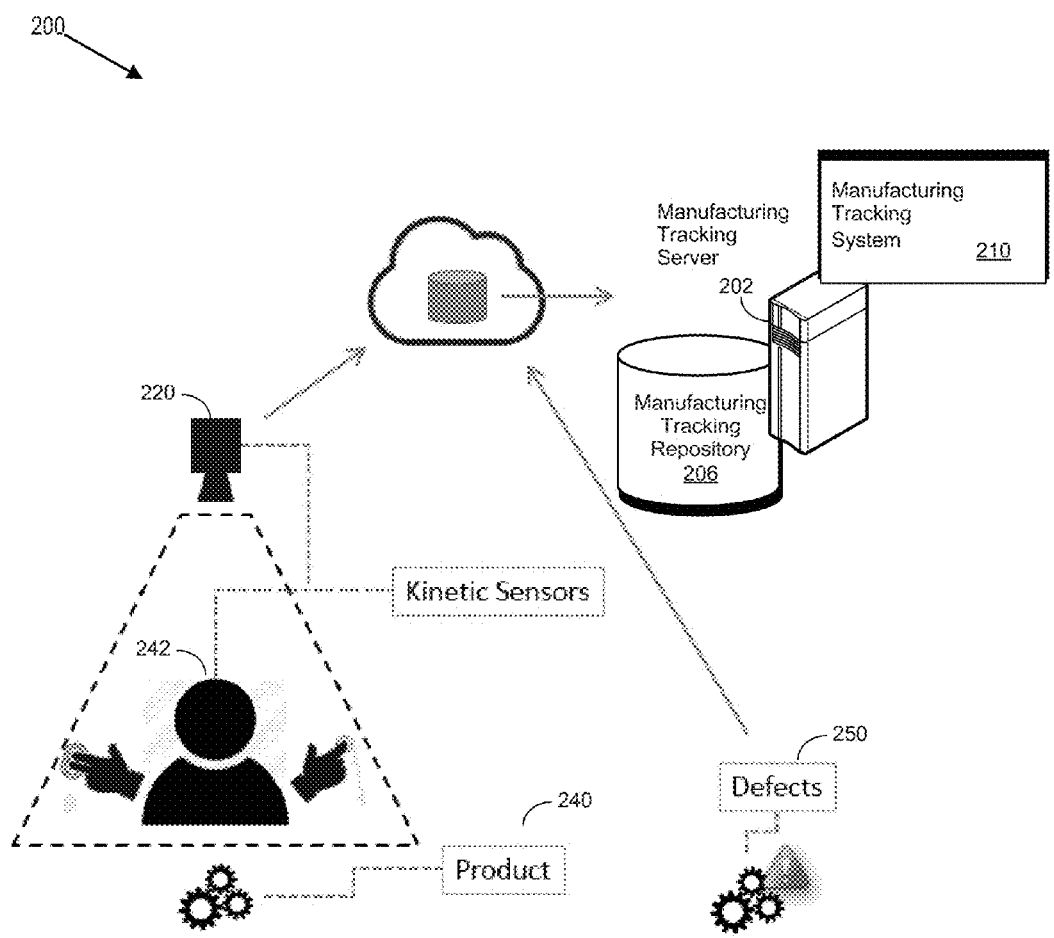
FIG. 2 is a simplified block diagram of a manufacturing environment.

Referring to FIG. 2, a simplified block diagram of a manufacturing environment 200 is shown. The environment 200 includes a manufacturing tracking server 202 which includes a manufacturing tracking system 210 and a manufacturing tracking information repository 206 (e.g., a database). In certain embodiments, the manufacturing tracking system 210 comprises some or all of the manufacturing tracking module 150.

The environment 200 further includes one or more motion sensing devices 220 (e.g., kinetic sensors). The motion sensing devices provide information to the manufacturing tracking system 210 via a network such as network 140. The environment 200 further includes one or more products 240 being manufactured by one or more assemblers 242. The environment 200 further includes defect information 250 which is provided to the manufacturing tracking system 210 via the network.

In various embodiments, some or all of the motion sensing devices include a kinetic motion sensor and/or a camera. In various embodiments, one or more of the motion sensing devices 220 include wearable devices. In various embodiments, one or more of the motion sensing devices 220 include IoT type devices.

The manufacturing environment 200 is used for performing a manufacturing tracking operation via a manufacturing tracking system 210. The manufacturing tracking operation uses one or more motion sensing devices 220 (such as an IoT type kinetic sensor) in the manufacturing environment 200 where items are manually assembled. The motion sensing devices 220 track repeated motions of the assembler. The motion sensing devices 220 tracks the motion at all times and associates the tracking information to an item manufactured by the assembler. Quality control on the item is also associated with the assembler. The manufacturing tracking operation then applies analytics to determine whether certain motions are causing the defective parts. The manufacturing tracking operation also correlates certain identified motions with certain defects. Such a correlation allows remediated action to be applied to decrease manufacturing defects in future manufacturing operations. The correlation information can also be applied to training of other assemblers.

Figure 3:
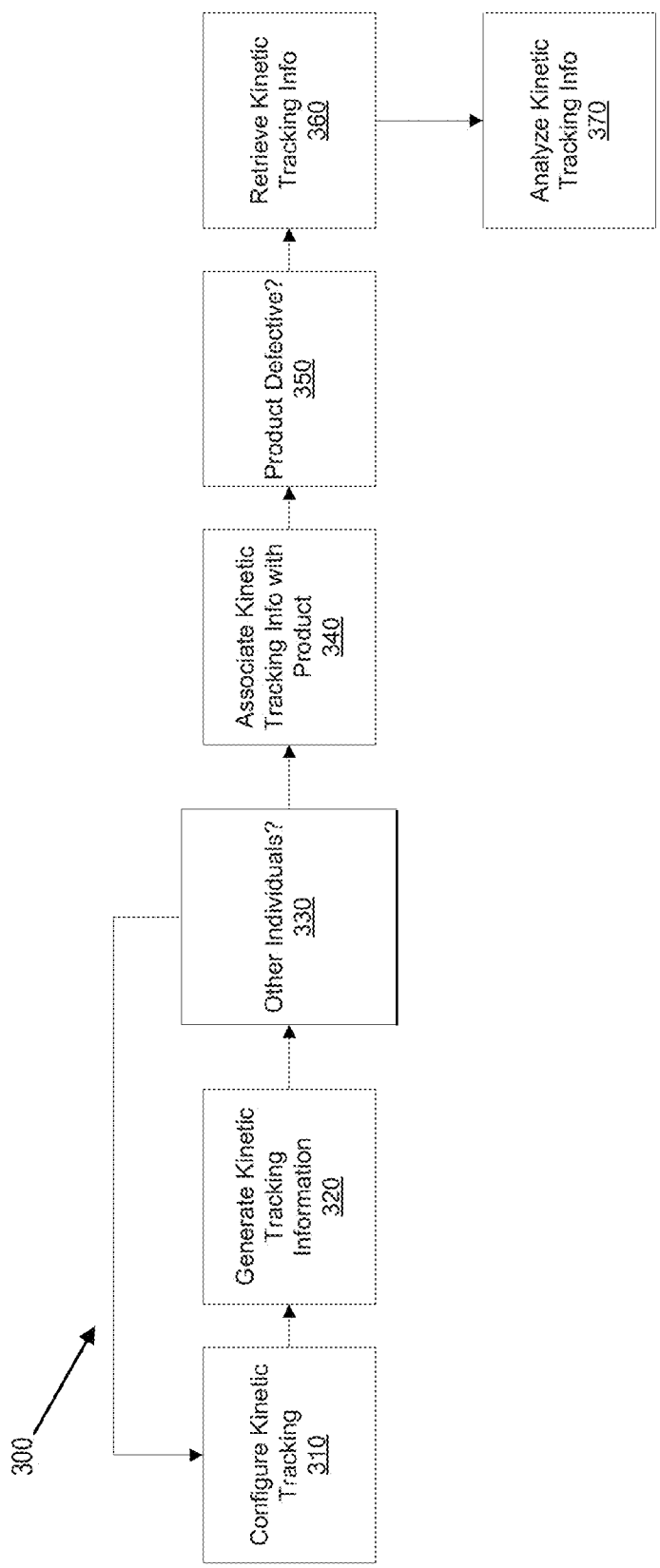
FIG. 3 shows a flow chart of a manufacturing tracking operation.

Referring to FIG. 3, a flow chart of a manufacturing tracking operation 300 is shown. More specifically, the manufacturing tracking operation begins at step 310 with configuring kinetic tracking for an individual. In certain embodiments, the configuring includes associating a kinetic tracking device with the individual. In certain embodiments, the configuring can also include associating other types of sensing devices such as one or more manual sensors, one or more cameras, etc. Next, at step 320, kinetic tracking information is generated during while the individual is performing their manual manufacturing steps. Next, at step 330, the manufacturing tracking operation determines whether other individuals are involved in the manufacturing of the item. If so, then the operation returns to step 310 to configure kinetic tracking for the next individual. If all individuals involved in the manufacturing of the item have been configured and tracked, then at step 340 the kinetic tracking information is associated with the item being manufactured and stored within a manufacturing tracking repository.

At step 350, if it is determined that an item is defective, such as via a quality control analysis, then the kinetic tracking information associated with the item is retrieved at step 360. The kinetic tracking information associated with the item is analyzed at step 370. This analysis can include identifying a standard range of motion for items produced with quality and a standard range of motion for items produced with defects and performing a comparison of the ranges of motion.

Figure 4:
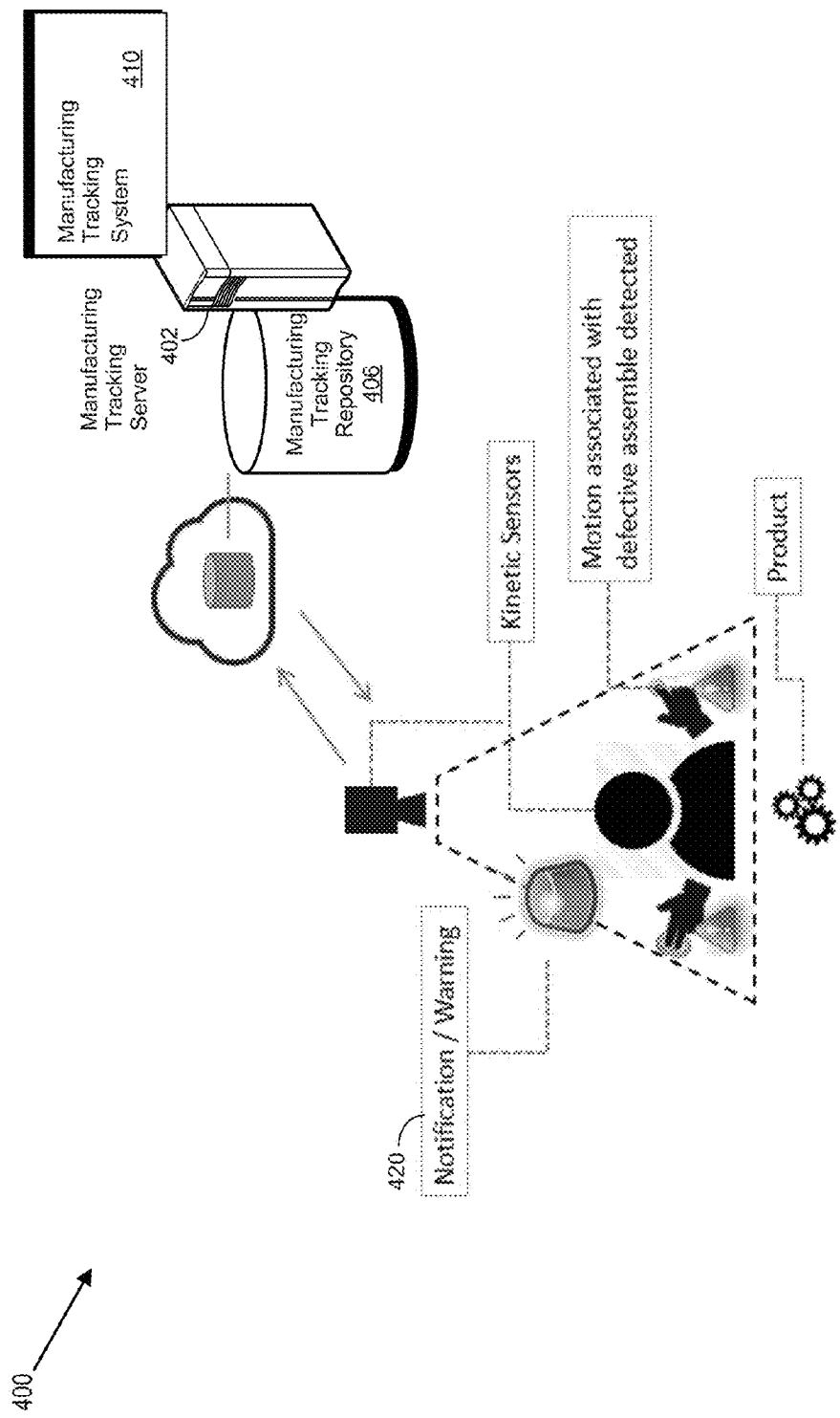
FIG. 4 is a simplified block diagram of a manufacturing environment.

Referring to FIG. 4, a simplified block diagram of a manufacturing environment 400 is shown. With the environment 400, the manufacturing tracking system 410 (which executes on a manufacturing tracking server 402 and includes a manufacturing tracking repository 406) includes a baseline tracking function. With the baseline tracking function, the manufacturing tracking system 410 sets a baseline with respect to a range of motions that produce items of quality. An additional step can be added into the manufacturing tracking operation 300 to generate a warning 420 when kinetic tracking information for an individual does not meet the baseline range of motions. Additionally, in certain embodiments, a risk analysis can be performed based on the kinetic tracking information to identify a level of risk of a defective product based on historical kinetic tracking information.

Additionally, in certain embodiments, the manufacturing tracking operation can be used to track defective parts in general. More specifically, if a specific product or component begins to experience defects from the field (i.e., after the product is deployed), then information obtained during the manufacturing tracking operation can be used to aid in determining how the product was assembled and whether the assembly is contributing to the defect. If the information indicates that the product was properly assembled, then this information can be used to narrow down a cause of the defect by removing questions regarding whether the product were properly assembled from the analysis.

Although the present invention has been described in detail, it should be understood that various changes, substitutions and alterations can be made hereto without departing from the spirit and scope of the invention as defined by the appended claims.

What is claimed is:

1. A method for tracking manufacturing steps, comprising:
   tracking, via a kinetic sensor, kinetic movements of an assembler over a period of time to provide kinetic tracking information, the kinetic movements comprising product assembly movements;
   storing the kinetic tracking information in a kinetic tracking information repository;
   identifying, via a processor, a defect in an item manufactured during the period of time;
   analyzing, via the processor, the kinetic tracking information to determine whether the kinetic movements of the assembler contributed to the defect;
   associating a first range of motion for items produced without defects and a second range of motion for items produced with defects; and,
   warning the assembler when the kinetic movements of the assembler fall within the second range of motion.

2. The method of claim 1, wherein: the kinetic sensor comprises a motion sensing device.

3. The method of claim 2, wherein:
   the motion sensing device comprises an Internet of Things (IoT) type device.

4. The method of claim 2, wherein: the tracking kinetic movements is performed at least in part via the kinetic sensor.

5. The method of claim 1, further comprising:
   identifying a level of risk for movement within the second range of motion based on said associated items produced with defects.

6. A system comprising:
   a processor;
   a data bus coupled to the processor; and
   a non-transitory, computer-readable storage medium embodying computer program code, the non-transitory, computer-readable storage medium being coupled to the data bus, the computer program code interacting with a plurality of computer operations and comprising instructions executable by the processor and configured for:
   tracking, via a kinetic sensor, kinetic movements of an assembler over a period of time to provide kinetic tracking information, the kinetic movements comprising product assembly movements;
   storing the kinetic tracking information in a kinetic tracking information repository;
   identifying, via the processor, a defect in an item manufactured during the period of time;
   analyzing, via the processor, the kinetic tracking information to determine whether the kinetic movements of the assembler contributed to the defect
   associating a first range of motion for items produced without defects and a second range of motion for items produced with defects; and,
   warning the assembler when the kinetic movements of the assembler fall within the second range of motion.

7. The system of claim 6, wherein: the kinetic sensor comprises a motion sensing device.

8. The system of claim 7, wherein:
   the motion sensing device comprises an Internet of Things (IoT) type device.

9. The system of claim 7, wherein: the tracking kinetic movements is performed at least in part via the kinetic sensor.

10. The system of claim 6, wherein the instructions are further configured for: identifying a level of risk for movement within the second range of motion based on said associated items produced with defects.

11. A non-transitory, computer-readable storage medium embodying computer program code, the computer program code comprising computer executable instructions configured for:
 tracking, via a kinetic sensor, kinetic movements of an assembler over a period of time to provide kinetic tracking information, the kinetic movements comprising product assembly movements;
 storing the kinetic tracking information in a kinetic tracking information repository;
 identifying, via a processor, a defect in an item manufactured during the period of time;
 analyzing, via the processor, the kinetic tracking information to determine whether the kinetic movements of the assembler contributed to the defect;
 associating a first range of motion for items produced without defects and a second range of motion for items produced with defects; and,
 warning the assembler when the kinetic movements of the assembler fall within the second range of motion.

12. The non-transitory, computer-readable storage medium of claim 11, wherein: the kinetic sensor comprises a motion sensing device.

13. The non-transitory, computer-readable storage medium of claim 12, wherein:
 the motion sensing device comprises an Internet of Things (IoT) type device.

14. The non-transitory, computer-readable storage medium of claim 12, wherein: the tracking kinetic movements is performed at least in part via the kinetic sensor.

15. The non-transitory, computer-readable storage medium of claim 11, wherein the computer executable instructions are further configured for: identifying a level of risk for movement within the second range of motion based on said associated items produced with defects.

* * * * *